(12) United States Patent
Kim

(10) Patent No.: US 11,504,688 B2
(45) Date of Patent: *Nov. 22, 2022

(54) EXTENDED RELEASE MICROPARTICLES COMPRISING DRUG, AND PREPARATION METHOD THEREFOR

(71) Applicant: INVENTAGE LAB INC., Seongnam-si (KR)

(72) Inventor: Ju Hee Kim, Seongnam-si (KR)

(73) Assignee: INVENTAGE LAB INC., Seongnam-si (KR)

( * ) Notice: Subject to any disclaimer, the term of this patent is extended or adjusted under 35 U.S.C. 154(b) by 320 days.

This patent is subject to a terminal disclaimer.

(21) Appl. No.: 16/757,604

(22) PCT Filed: Oct. 16, 2018

(86) PCT No.: PCT/KR2018/012180
§ 371 (c)(1),
(2) Date: Apr. 20, 2020

(87) PCT Pub. No.: WO2019/078583
PCT Pub. Date: Apr. 25, 2019

(65) Prior Publication Data
US 2020/0261878 A1    Aug. 20, 2020

Related U.S. Application Data

(63) Continuation of application No. 15/788,906, filed on Oct. 20, 2017, now Pat. No. 10,843,159, and a
(Continued)

(51) Int. Cl.
*B01J 13/06* (2006.01)
*A61K 9/00* (2006.01)
(Continued)

(52) U.S. Cl.
CPC .............. *B01J 13/06* (2013.01); *A61K 9/0019* (2013.01); *A61K 9/146* (2013.01); *A61K 9/1647* (2013.01);
(Continued)

(58) Field of Classification Search
None
See application file for complete search history.

(56) References Cited

U.S. PATENT DOCUMENTS 6,277,391 B1    8/2001  Seo et al.
10,632,442 B2 *  4/2020  Kim .................. A61K 9/1647
(Continued)

FOREIGN PATENT DOCUMENTS

CN    103386118 A      11/2013
CN    104288122 A  *   1/2015
(Continued)

OTHER PUBLICATIONS

Google Patents. English Translation of CN 104288122 A. Obtained from https://patents.google.com/patent/CN104288122A/en?oq=microchannels+plga+microparticle on Jun. 28, 2022, originally published in Chinese on Jan. 21, 2015, pp. 1-7. (Year: 2015).*
(Continued)

*Primary Examiner* — Isaac Shomer
(74) *Attorney, Agent, or Firm* — STIP Law Group, LLC

(57) ABSTRACT

The present invention relates to extended release microparticles comprising a drug, and a preparation method therefor, and when the extended release microparticles comprising a drug are administered in order to replace conventional drugs that should be administered daily or monthly, the drug administration effect can be continuously maintained for one week to three months.
In addition, the drug administration effect is maintained for a long time and, simultaneously, microparticles are prepared
(Continued)

so as to have the average diameter of a fixed micro-size, and thus an effective drug concentration can be constantly maintained by controlling the release of the drug from the microparticles, and a foreign body sensation and pain can be reduced during drug administration since microparticles having a uniform size are included during application as an injectable drug.

1 Claim, 8 Drawing Sheets

Related U.S. Application Data continuation of application No. 15/788,930, filed on Oct. 20, 2017, now Pat. No. 10,632,442.

(51) Int. Cl.
 B01J 19/00 (2006.01)
 A61K 9/16 (2006.01)
 B01F 33/302 (2022.01)
 B01F 33/30 (2022.01)
 B01F 33/3011 (2022.01)
 A61K 9/14 (2006.01)
 A61K 31/365 (2006.01)
 A61K 31/58 (2006.01)
 B01L 3/00 (2006.01)
 C08J 5/00 (2006.01)
 B01J 2/06 (2006.01)
 B01J 2/02 (2006.01)

(52) U.S. Cl.
 CPC .......... A61K 9/1682 (2013.01); A61K 31/365 (2013.01); A61K 31/58 (2013.01); B01F 33/30 (2022.01); B01F 33/302 (2022.01); B01F 33/3011 (2022.01); B01J 19/0093 (2013.01); B01L 3/502707 (2013.01); C08J 5/00 (2013.01); B01J 2/02 (2013.01); B01J 2/06 (2013.01); B01J 2219/00889 (2013.01); B01L 2200/0647 (2013.01); B01L 2300/0816 (2013.01); B01L 2300/161 (2013.01); C08J 2367/04 (2013.01)

(56) References Cited

U.S. PATENT DOCUMENTS

| 10,843,159 | B2* | 11/2020 | Kim | A61K 9/0019 |
|---|---|---|---|---|
| 11,344,624 | B2* | 5/2022 | Kim | A61K 9/5084 |
| 11,400,085 | B2* | 8/2022 | Kim | A61K 9/0019 |
| 2003/0125237 | A1* | 7/2003 | Kim | A61K 9/5089 |
| | | | | 424/491 |
| 2011/0160218 | A1* | 6/2011 | Holmes | A61K 31/365 |
| | | | | 514/250 |
| 2013/0224257 | A1* | 8/2013 | Sah | A61K 9/1647 |
| | | | | 514/383 |
| 2014/0148350 | A1* | 5/2014 | Spetzler | G01N 33/574 |
| | | | | 436/501 |
| 2017/0056523 | A1* | 3/2017 | Roffler | C07K 16/30 |

FOREIGN PATENT DOCUMENTS

| JP | 2006528179 A | 12/2006 |
|---|---|---|
| JP | 2008539260 A | 11/2008 |
| KR | 20000000942 A | 1/2000 |
| KR | 1020000000942 A | 1/2000 |
| KR | 20010099583 A | 11/2001 |
| KR | 1020010099583 A | 11/2001 |
| KR | 1020070094009 A | 9/2007 |
| KR | 20110121320 A | 11/2011 |
| KR | 1020110121320 A | 11/2011 |

OTHER PUBLICATIONS

George Crotts and Tae Gwan Park, Stability and release of bovine serum albumin encapsulated within poly(D,L-lactide-co-glycolide) microparticles, Journal of controlled release, 1997, pp. 123-134, vol. 44, Elsevier Science Ireland Ltd, Amsterdam, Netherlands.
Leonard N. Nell et al, Thermally Induced Denaturation of Lyophilized Bovine Somatotropin and Lysozyme As Impacted by Moisture and Excipients, Journal of Pharmaceutical Sciences, Jun. 1995, pp. 707-712, vol. 84, Issue 6, Elsevier, Amsterdam, Netherlands.
International Search Report of PCT/KR2018/012180, dated Jan. 15, 2019, English translation.
Koji Kinoshita et al, From Single Microparticles to Microfluidic Emulsification: Fundamental Properties (Solubility, Density, Phase Separation) from Micropipette Manipulation of Solvent, Drug and Polymer Microspheres, Processes, Nov. 30, 2016, pp. 1-28, vol. 4, issue 49, MDPI, Basel, Switzerland.

* cited by examiner

[FIG. 1]
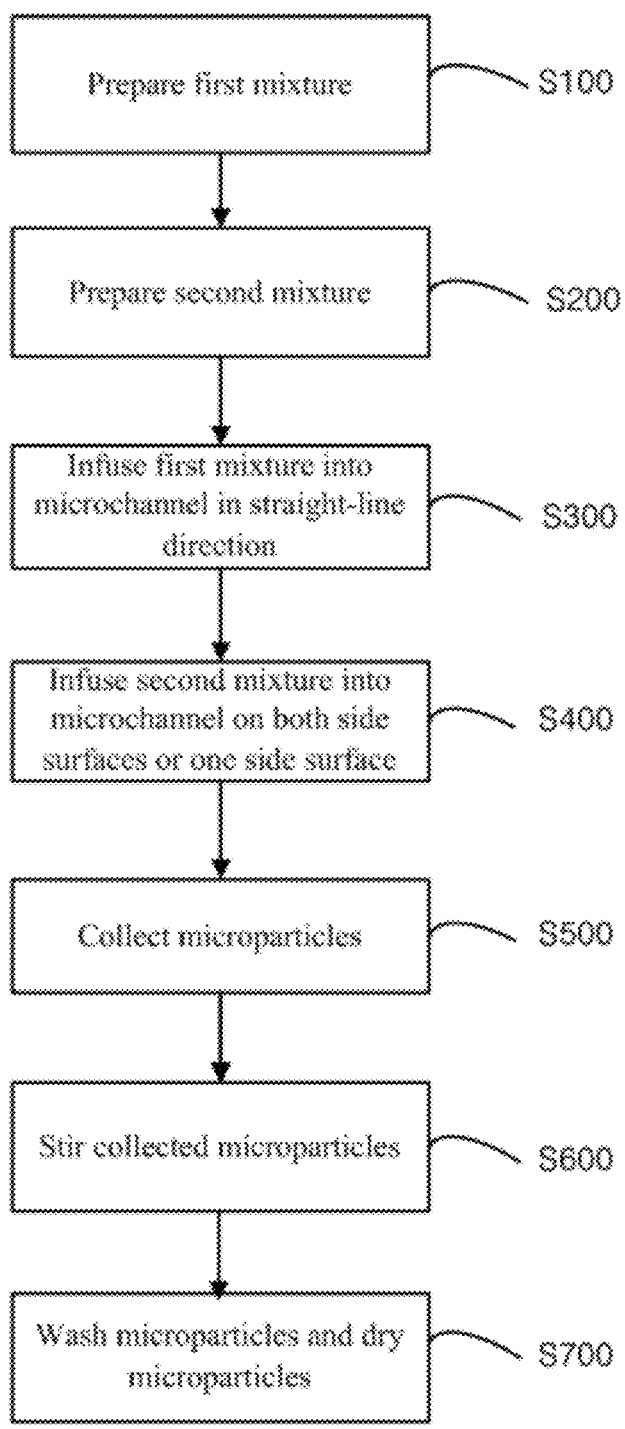

[FIG. 2]
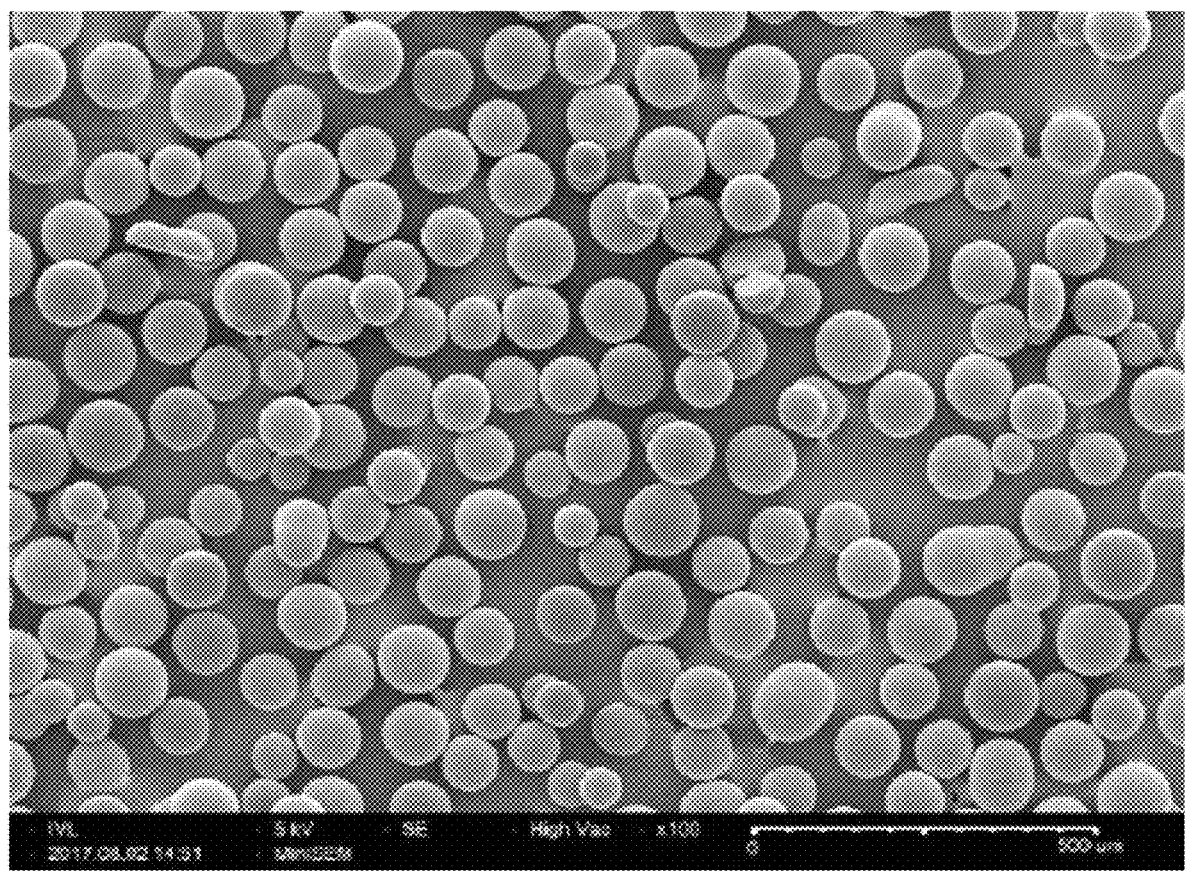

[FIG. 3]
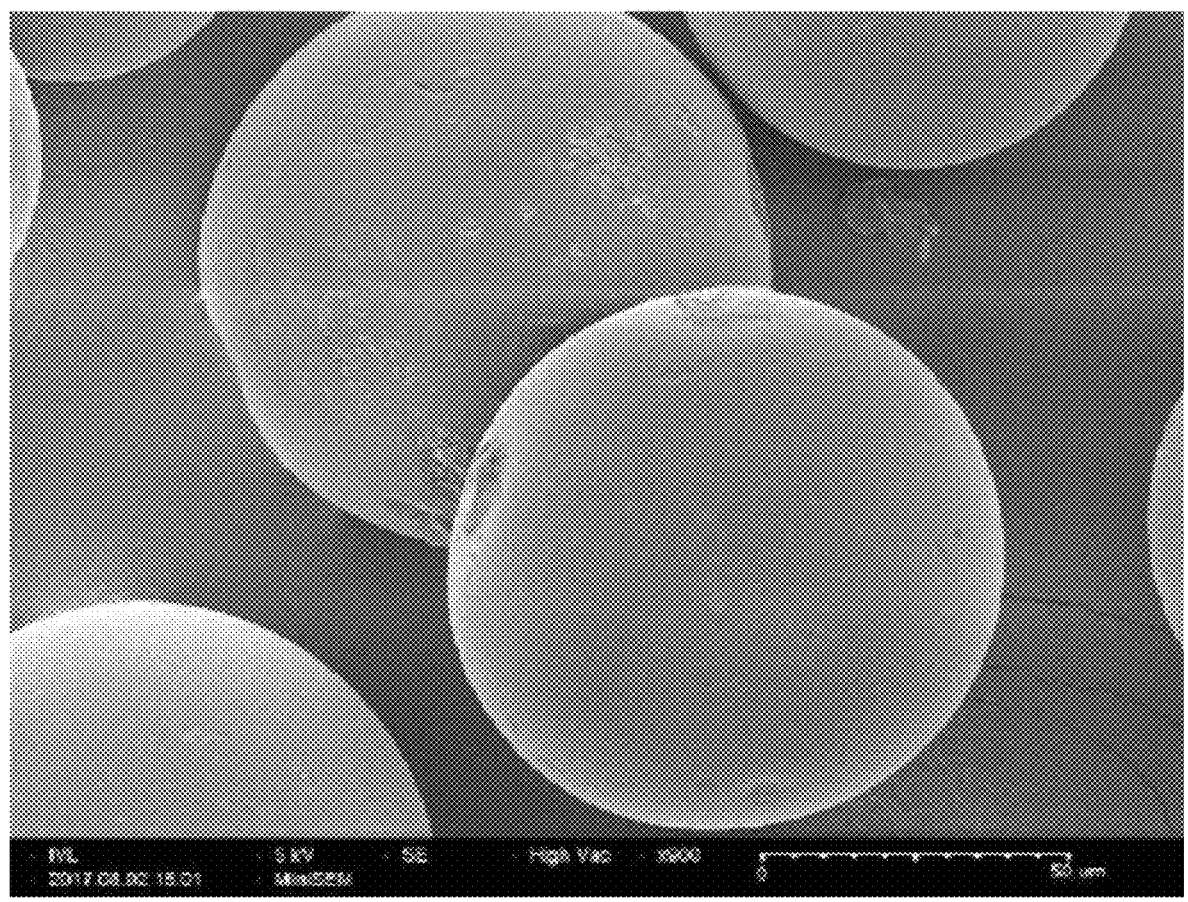

[FIG. 4]
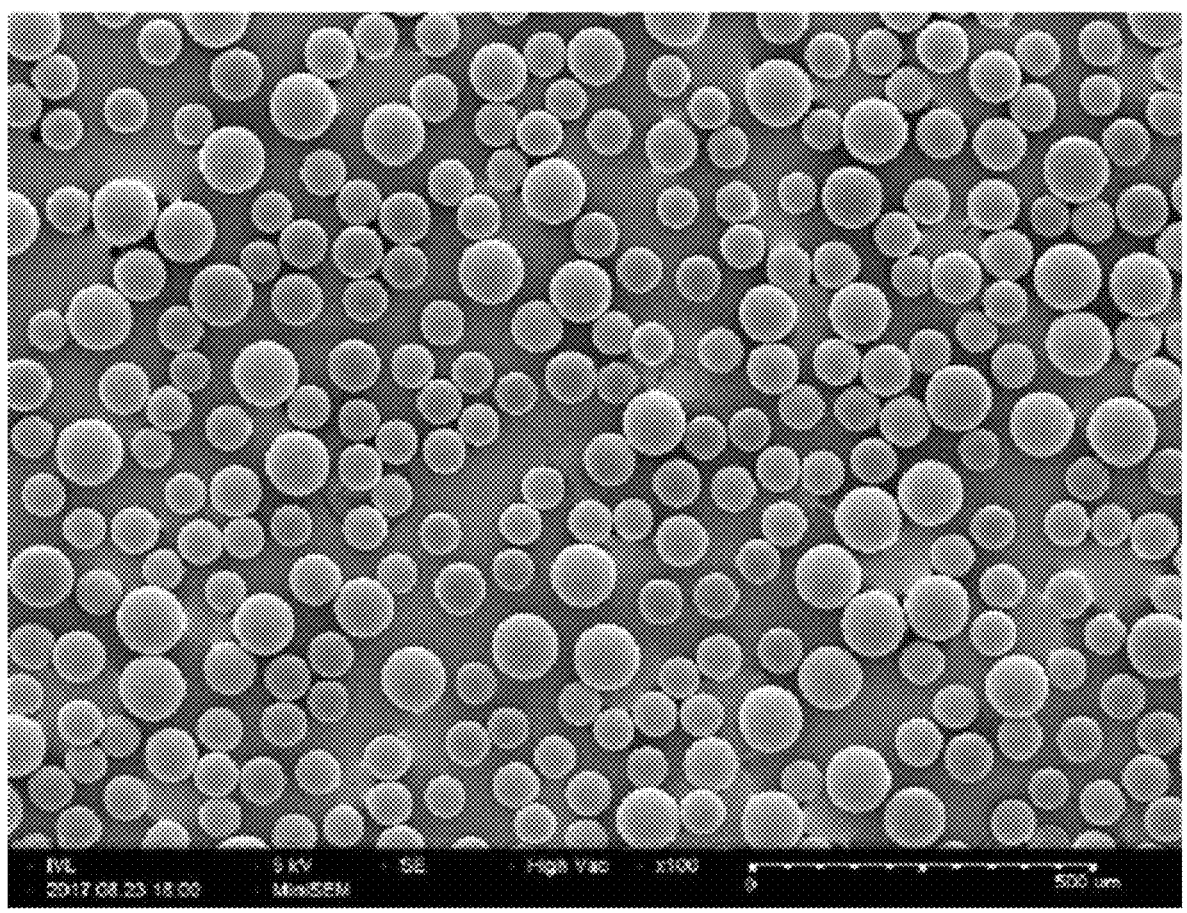

[FIG. 5]
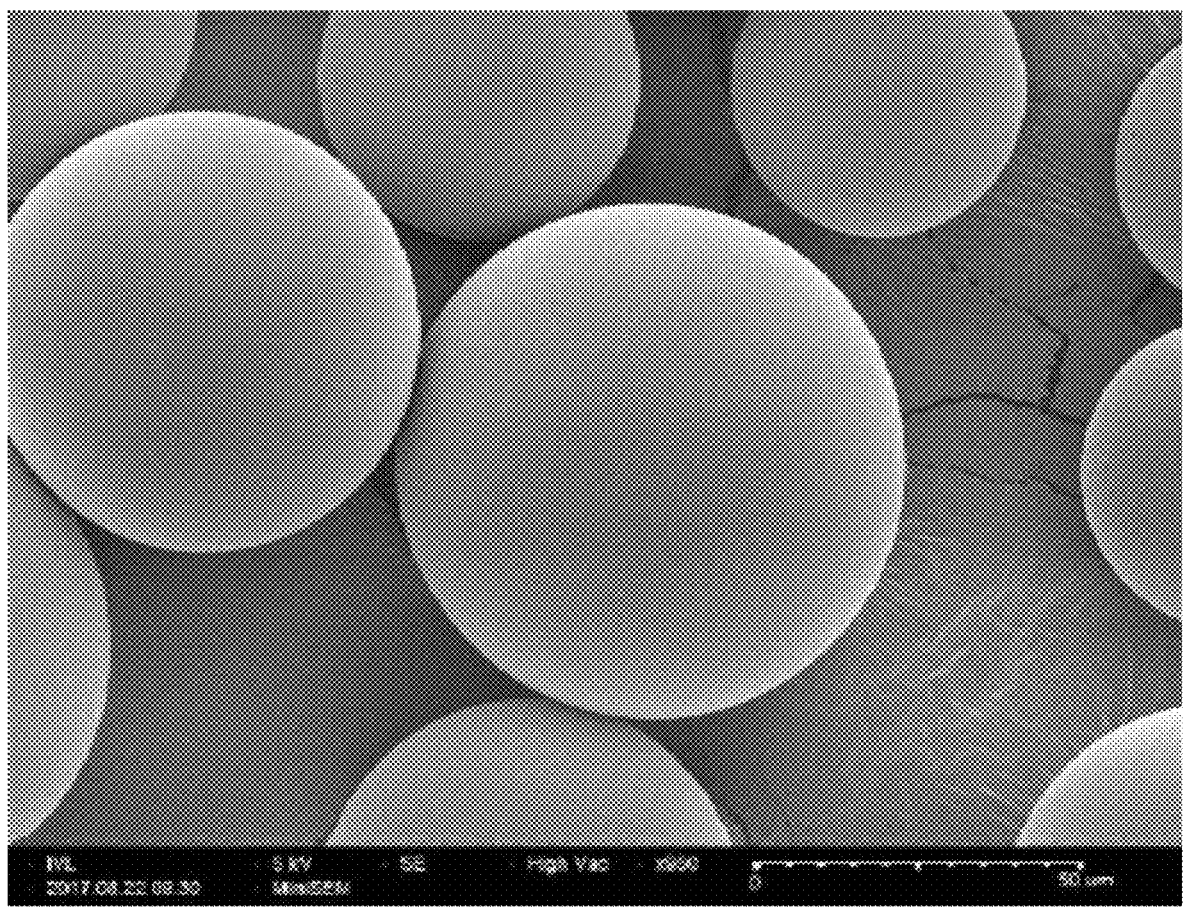

[FIG. 6]
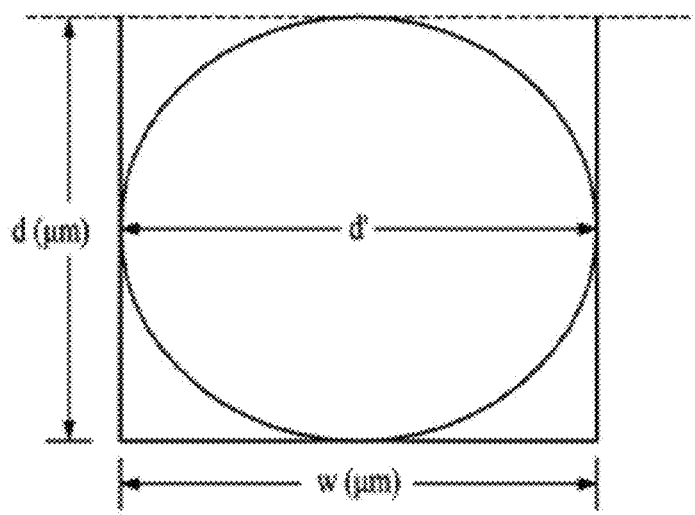
[FIG. 7]
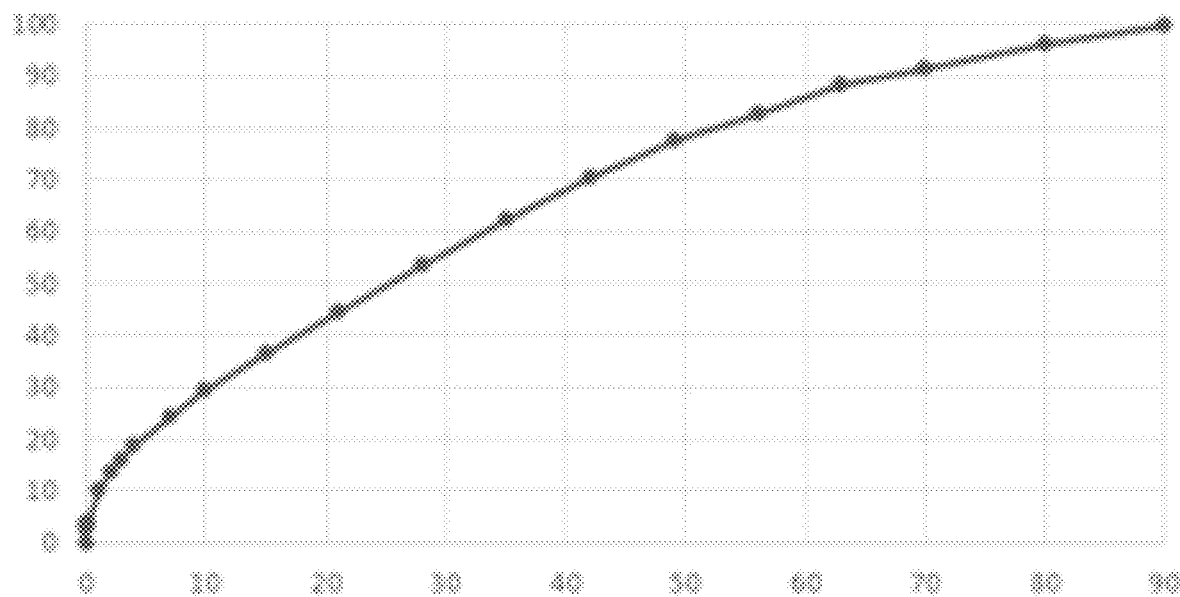

[FIG. 8]
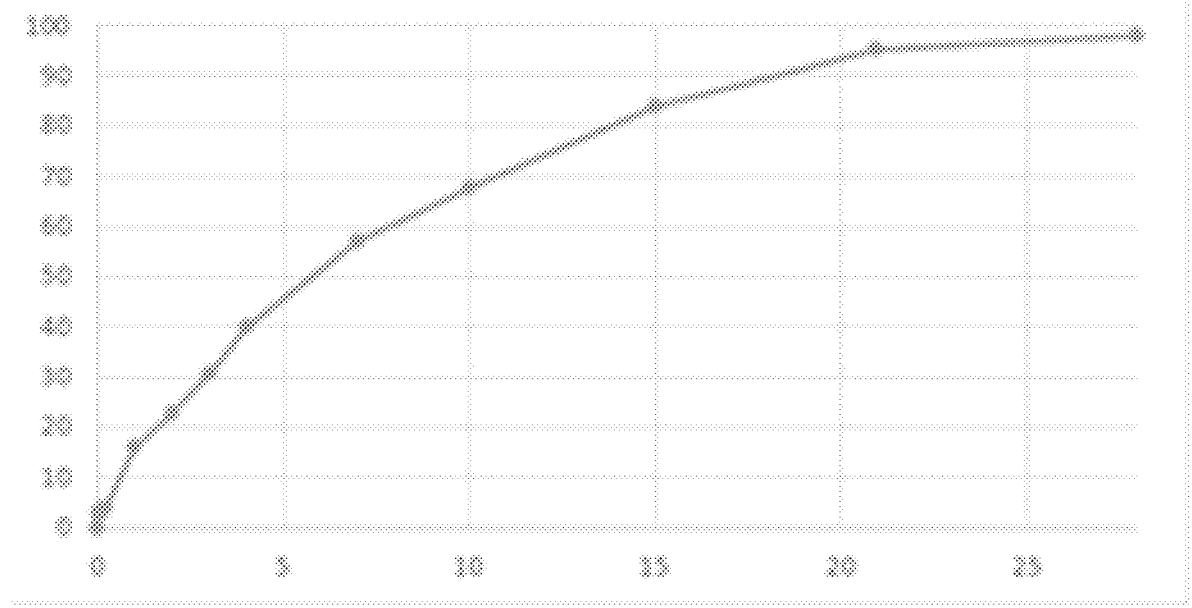
[FIG. 9]
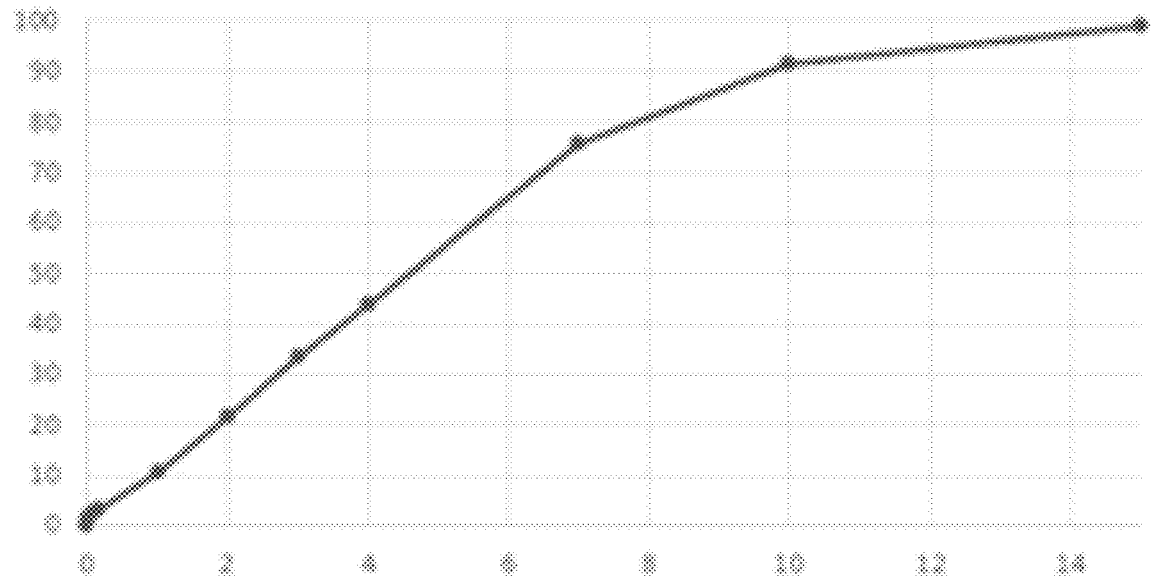

[FIG. 10]
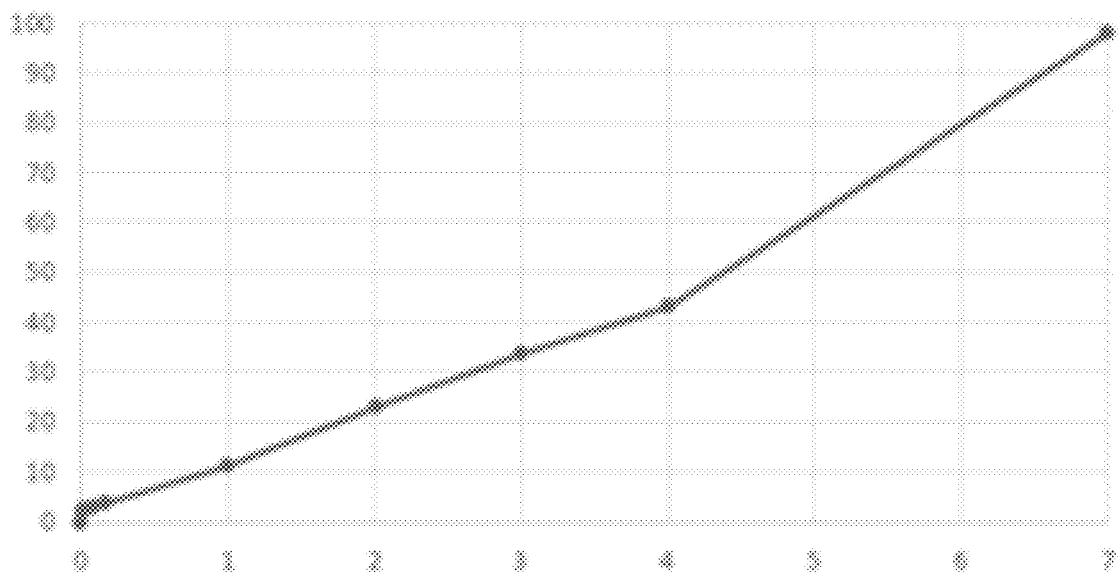

EXTENDED RELEASE MICROPARTICLES COMPRISING DRUG, AND PREPARATION METHOD THEREFOR

CROSS-REFERENCE TO RELATED APPLICATIONS

This application is the U.S. National Phase under 35 U.S.C. § 371 of International Application No. PCT/KR2018/012180 filed on Oct. 16, 2018, which in turn claims the benefit of U.S. application Ser. No. 15/788,906 filed on Oct. 20, 2017, and Ser. No. 15/788,930 filed on Oct. 20, 2017, the disclosures of which are incorporated by reference into the present application.

TECHNICAL FIELD

The present invention relates to extended release microparticles comprising a drug, and a preparation method therefor, and more particularly to extended release microparticles comprising a drug which is contained in the microparticles comprising a biodegradable polymer and capable of sustaining the drug effect due to the drug for a long time by continuously releasing the drug in the body, and a preparation method therefor.

BACKGROUND ART

In general, the majority of protein and peptide drugs lose their active structure in the acidic environment of the stomach upon oral administration or are destroyed by enzymatic degradation and have a significantly low rate of absorption in the stomach or intestinal mucosa.

For this reason, most of the protein and peptide drugs are administered parenterally, that is, by an injection method. Most of the parenterally administered protein and peptide drugs need to be repeatedly injected continuously after administration due to short half-life and low bioavailability in vivo, and require long-term administration for several months in many cases.

In order to solve these problems, studies have been actively conducted on an extended and sustained release dosage form in which a drug is encapsulated in a biodegradable polymer carrier having a slow degradation property in vivo using a biodegradable polymer which releases protein and peptide drugs in vivo as the polymer is degraded.

Currently, aliphatic polyesters developed and used as polymeric carriers in protein and peptide drugs have already been recognized for their biocompatibility, approved by the U.S. Food and Drug Administration (FDA), and widely used in applications such as carriers for drug delivery or surgical sutures. Specific examples of the aliphatic polyesters include poly-L-lactic acid, polyglycolic acid, poly-D-lactic acid-co-glycolic acid, poly-L-lactic acid-co-glycolic acid, poly-D,L-lactic acid-co-glycolic acid (hereinafter, referred to as 'PLGA'), poly-caprolactone, poly-valerolactone, poly-hydroxybutyrate, poly-hydroxyvalerate, and the like.

Recently, as high molecular weight peptides or proteins, and the like have been developed as new therapeutic agents, various efforts to encapsulate and continuously release these drugs in a polymer carrier have been made, but a dosage form in which a protein drug is encapsulated in a microsphere including the aforementioned aliphatic polyester has big problems such as an initial burst effect of the drug, or an incomplete release in which the release rate of the drug is not adjusted at a predetermined rate for a predetermined period of time and 100% of the encapsulated drug is not released for effects of various factors.

For example, there are reports that a model protein drug such as bovine serum albumin and lysozyme has a final release rate of around 50% after a large amount of drug is released in the initial stage [Crotts, G. and Park, T. G., J. Control. Release, 44, 123-134, 1997; Leonard, N. B., Michael, L. H., Lee, M. M. Pharm. Sci., 84, 707-712], and when a recombinant human growth hormone is encapsulated in a microsphere using an aliphatic polyester as a carrier, 30 to 50% of the protein drug is released excessively in the initial stage, and then the amount of around 40 to 60% of the protein drug remains in the microsphere without being released.

As a general method for preparing microspheres, a phase separation method [U.S. Pat. No. 4,673,595], a spray-drying method, and an organic solvent evaporation method [U.S. Pat. No. 4,389,330] are known. The phase separation method has a disadvantage in that the process is complex, such as removal of all the used organic solvents because silicone oil, heptene, ethyl alcohol, and the like need to be used together in addition to a methylene chloride solvent, and the spray-drying method may cause denaturation of proteins and peptides by performing spray-drying at a high temperature of 60° C. or more with an organic solvent at high temperature. Therefore, generally, the organic solvent evaporation method is most commonly used for the preparation of protein and peptide microspheres.

In the preparation of sustained release microspheres containing proteins or peptides, there is a need for a preparation method which has no initial burst effect of the drug, has no incomplete release in which 100% of the drug is not released while maintaining the drug release at the zero order release regardless of the stable release period, has a simple preparation method, has a high encapsulation rate of the drug, has good stability of the encapsulated drug, and is economically efficient.

Further, in addition to protein and peptide drugs, studies on long-lasting dosage forms of drugs have been continued as a method for improving medication compliance to patients and stably administering drugs even in the case of existing synthetic medicines having low medication compliance.

Even in the case of synthetic medicines, as a drug delivery technique for controlling a drug to be administered in vivo such that the drug is not discharged instantaneously but discharged slowly at a predetermined rate, extended release and sustained release studies, such as a method of encapsulating a drug in a biodegradable polymer such as the protein and peptide drugs previously described, have been conducted.

Thus, even in the preparation of sustained release microspheres containing protein and peptide drugs and synthetic medicines, there is a need for studies on development of a preparation method which has a simple preparation method and a high encapsulation rate of the drug and is excellent in stability of the encapsulated drug and economically efficient.

PRIOR ART DOCUMENT

Patent Document (Patent Document 1) KR 10-2007-0094009 A1

DISCLOSURE

Technical Problem

An object of the present invention is to provide extended release microparticles comprising a drug, and a preparation method therefor.

Another object of the present invention is to provide sustained release microparticles capable of continuously maintaining a drug administration effect for 1 week to 3 months when the extended release microparticles comprising a drug are administered in order to replace a drug in the related art which needs to be administered daily or monthly, and a preparation method therefor.

Still another object of the present invention is to maintain the drug administration effect for a long time, to be able to constantly maintain an effective drug concentration by controlling the release of the drug from the microparticles as the microparticles are prepared so as to have the average particle diameter of a fixed micro-size, and to reduce a foreign body sensation and pain during drug administration since microparticles having a uniform size are included during application as an injectable drug.

Technical Solution

To achieve the objects, extended release microparticles comprising a drug according to an exemplary embodiment of the present invention are microparticles comprising a biodegradable polymer and a drug, in which the microparticles have a spherical shape including a biodegradable polymer, are in a form in which the drug is uniformly distributed in the spherical biodegradable polymer, and have a particle average diameter of 20 to 70 μm.

The drug may be selected from the group consisting of palonosetron, minocycline, liraglutide, exenatide, olanzapine, aripiprazole, donepezil, memantine, lanreotide, octreotide, and naltrexone.

The microparticles are injected into the body, and then the drug is released by the degradation of the biodegradable polymer, so that the drug effect may be continuously maintained.

The drug effect duration from the release of the drug is 1 week to 3 months.

The microparticle may include a biodegradable polymer and a drug at a weight ratio of 2:1 to 9:1.

The biodegradable polymer may be selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof.

The microparticles are prepared using a microchannel, and the width (w) of the channel cross-section may be in a ratio range of 0.7 to 1.3 with respect to an average diameter (d') of the microparticles.

A composition for treating and preventing emesis according to another exemplary embodiment of the present invention may include the microparticles.

An antimicrobial and anti-inflammatory composition according to still another exemplary embodiment of the present invention may include the microparticles.

A composition for preventing and treating diabetes according to yet another exemplary embodiment of the present invention may include the microparticles.

A composition for treating or preventing a psychiatric disorder according to still yet another exemplary embodiment of the present invention may include the microparticles.

A composition for preventing and treating dementia according to a further exemplary embodiment of the present invention may include the microparticles.

A composition for preventing and treating acromegaly according to another further exemplary embodiment of the present invention may include the microparticles.

A composition for preventing and treating alcoholism according to still another further exemplary embodiment of the present invention may include the microparticles.

A method for preparing extended release microparticles comprising a drug according to yet another further exemplary embodiment of the present invention includes: 1) preparing a first mixture by dissolving a biodegradable polymer and a drug in an organic solvent; 2) preparing a second mixture by dissolving a surfactant in water; 3) infusing the first mixture in Step 1) into a microchannel in a straight-line direction and allowing the first mixture to flow; 4) preparing microparticles in a form in which a drug is uniformly distributed in spherical biodegradable polymer particles by infusing the second mixture in Step 2) into a microchannel formed on both side surfaces or one side surface and allowing the second mixture to flow so as to form an intersection point with a microchannel through which the first mixture in Step 3) flows in a straight-line direction, and intersecting a flow of the first mixture in a straight-line direction with a flow of the second mixture; 5) collecting the microparticles produced at the intersection point in Step 4); 6) evaporating and removing an organic solvent present in the microparticles collected in Step 5) by stirring the microparticles; and 7) washing the microparticles in Step 6) and drying the microparticles, in which the drug may be selected from the group consisting of palonosetron, minocycline, liraglutide, exenatide, olanzapine, aripiprazole, donepezil, memantine, lanreotide, octreotide, and naltrexone.

Step 6) may include: 6-1) firstly stirring the microparticles at a rate of 800 to 1,200 rpm at 14 to 16° C. for 1 to 2 hours; 6-2) secondly stirring the microparticles at a rate of 800 to 1,200 rpm at 19 to 21° C. for 0.5 to 1.5 hours after the first stirring; and Step 6-3) thirdly stirring the microparticles at a rate of 800 to 1200 rpm at 24 to 26° C. for 0.5 to 1.5 hours after the second stirring.

Advantageous Effects

The present invention relates to extended release microparticles comprising a drug, and a preparation method therefor, and when the extended release microparticles comprising a drug are administered in order to replace conventional drugs that should be administered daily or monthly, the drug administration effect can be continuously maintained for one week to three months.

In addition, the drug administration effect is maintained for a long time and, simultaneously, microparticles are prepared so as to have the average diameter of a fixed micro-size, and thus an effective drug concentration can be constantly maintained by controlling the release of the drug from the microparticles, and a foreign body sensation and pain can be reduced during drug administration since microparticles having a uniform size are included during application as an injectable drug.

DESCRIPTION OF DRAWINGS

FIG. 1 is a flowchart of the method for preparing extended release microparticles comprising a drug according to an exemplary embodiment of the present invention.

FIG. 2 is an SEM photograph of microparticles by the preparation method according to an exemplary embodiment of the present invention.

FIG. 3 is an SEM photograph of microparticles by the preparation method according to an exemplary embodiment of the present invention.

FIG. 4 is an SEM photograph of microparticles by the preparation method according to an exemplary embodiment of the present invention.

FIG. 5 is an SEM photograph of microparticles by the preparation method according to an exemplary embodiment of the present invention.

FIG. 6 is a view on the relationship between an average diameter of microparticles and a cross-section of a microchannel.

FIG. 7 illustrates a result of an in-vitro drug release experiment on microparticles containing palonosetron.

FIG. 8 illustrates a result of an in-vitro drug release experiment on microparticles.

FIG. 9 illustrates a result of an in-vitro drug release experiment on microparticles.

FIG. 10 illustrates a result of an in-vitro drug release experiment on microparticles.

BEST MODE

Hereinafter, the Examples of the present invention will be described in detail such that a person skilled in the art to which the present invention pertains can easily carry out the present invention. However, the present invention can be implemented in various different forms, and is not limited to the Examples described herein.

The emesis of the present invention means nausea or emesis, which is one of the symptoms which may be caused by various conditions, and in an exemplary embodiment, nausea or emesis is a side effect of viral gastroenteritis in a subject. In an exemplary embodiment, nausea or emesis is a side effect of bacterial gastroenteritis in a subject. In an exemplary embodiment, nausea or emesis is a side effect of gastritis (gastric wall inflammation) in a subject. In an exemplary embodiment, nausea or emesis is a side effect of inflammatory bowel disease in a subject. In an exemplary embodiment, nausea or emesis is a side effect of irritable bowel syndrome in a subject. In an exemplary embodiment, nausea or emesis is a side effect of cholecystitis in a subject. In an exemplary embodiment, nausea or emesis is a side effect of dyspepsia in a subject. In an exemplary embodiment, nausea or emesis is a side effect of pancreatitis in a subject. In an exemplary embodiment, nausea or emesis is a side effect of appendicitis in a subject. In an exemplary embodiment, nausea or emesis is a side effect of a surgical intervention in a subject. In an exemplary embodiment, nausea or emesis is a side effect of hepatitis in a subject. In an exemplary embodiment, nausea or emesis is a side effect of peritonitis in a subject. In an exemplary embodiment, nausea or emesis is a side effect of gastroesophageal reflux disease in a subject. In an exemplary embodiment, nausea or emesis is a side effect of intestinal obstruction in a subject. In an exemplary embodiment, nausea or emesis is a side effect of food poisoning in a subject. In an exemplary embodiment, nausea or emesis is a side effect of tumors in a subject. The antimicrobial and anti-inflammation of the present invention means the use of antibiotics caused by infection of various pathogens and the control of diseases of domestic animals including humans, and is not limited to the examples, and means all of the antibiotics used for diseases caused by infection.

The diabetes of the present invention is a chronic metabolic disease, and is a disease that causes vascular disorders and dysfunctions of nerves, kidneys, and retinas over a long period of time, and results in the loss of life. Diabetes is largely divided into insulin-dependent diabetes (type 1 diabetes) and non-insulin-dependent diabetes (type 2 diabetes) according to the occurring mechanism, and in the present invention, the diabetes preferably means non-insulin-dependent diabetes. The non-insulin-dependent diabetes generally shows resistance to insulin, and the hyperglycemic state usually continues due to the dysfunction of insulin. Since chronic hyperglycemia damages the pancreatic beta cells to cause cell death, it requires an effective glycemic control to treat type 2 diabetes.

The psychiatric disorder of the present invention means a mental state such as schizophrenia, schizophreniform disorder, and acute mania, and means a disease selected from the group consisting of schizophrenia and related psychoses, bipolar mania, bipolar disorder, seizure, obsessive-compulsive disorder, generalized anxiety disorder, post traumatic stress syndrome, extreme shyness, diabetic nerve pain, and depression.

The dementia of the present invention is a word derived from Latin and has a meaning of 'out of mind'. The lack of intellectual ability since birth is called 'mental retardation', while dementia is a condition in which a person who has lived normally has impaired brain function due to various causes, thereby exhibiting considerable obstacles to daily life due to persistent and general deterioration in cognitive function compared to before. Here, the cognitive function refers to various intellectual abilities such as memory ability, linguistic ability, time and space grasping ability, judgment ability, and abstract thinking ability, and each cognitive function is closely related to a specific brain region. The causative diseases that induces the clinical syndrome called dementia may be each subdivided into about 70 types. Among the various dementia-causing diseases, the most common are 'Alzheimer's disease' and 'vascular dementia', but in addition, dementia may be caused by degenerative brain diseases such as dementia with Lewy bodies and Parkinson's disease, and a wide variety of causative diseases, such as normal pressure hydrocephalus, head trauma, brain tumor, metabolic disease, deficiency disease, addictive disease, and infectious disease.

The acromegaly of the present invention is a disease in which the shape of the face gradually changes while the hands and feet become thicker and the forehead and chin protrude, and means a condition in which the growth hormone is secreted a lot in all grown adults, but the heights of the adults do not increase any more and only the terminal parts become thicker.

The alcoholism of the present invention means a state of 'loss of regulation ability' for liquor (alcohol), and means alcoholism due to 'alcohol abuse' and 'alcohol dependence'.

FIG. 1 is a flowchart of the method for preparing extended release microparticles comprising a drug of the present invention.

According to the aforementioned flowchart, the preparation of the extended release microparticles comprising a drug of the present invention proceeds in the order of 1) preparing a first mixture (S100); 2) preparing a second mixture (S200); 3) infusing the first mixture into a microchannel in a straight-line direction (S300); 4) infusing the second mixture into a microchannel on both side surfaces or one side surface (S400); 5) collecting the microparticles (S500); stirring the collected microparticles (S600); and washing the microparticles and drying the microparticles (S700).

More specifically, the method for preparing extended release microparticles comprising a drug according to an exemplary embodiment of the present invention will be described as follows.

Step 1) (S100) is a step of preparing a first mixture, specifically a step of preparing a first mixture by dissolving a biodegradable polymer and a drug in an organic solvent, in which the biodegradable polymer is selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide) (PLGA), but the biodegradable polymer is not limited to the example.

Further, the organic solvent is an organic solvent which is immiscible with water, is one or more selected from the group consisting of, for example, chloroform, chloroethane, dichloroethane, trichloroethane, and a mixture thereof, and is preferably dichloromethane, but the organic solvent is not limited to the example, and the organic solvent is a solvent which can dissolve a biodegradable polymer and a drug, and is not limited to the aforementioned example but any organic solvent can be used as long as the organic solvent may be easily selected by a person with ordinary skill in the art.

The drug may be selected from the group consisting of palonosetron, minocycline, liraglutide, exenatide, olanzapine, aripiprazole, donepezil, memantine, lanreotide, octreotide, and naltrexone.

More specifically, it is possible to use palonosetron which is an antiemetic, minocycline which is an antibiotic, liraglutide and exenatide for preventing and treating diabetes, olanzapine and aripiprazole for preventing and treating a psychosis, donepezil and memantine for preventing and treating dementia, lanreotide and octreotide for preventing and treating acromegaly, and naltrexone for preventing and treating alcoholism as a drug for preparing extended release microparticles.

Step 1) (S100) prepares a first mixture in which a biodegradable polymer and a drug are dissolved, and as the solvent, an organic solvent is used as described above. The drug and the biodegradable polymer are completely dissolved by using an organic solvent using dissolution characteristics of the drug and the biodegradable polymer.

After the drug and the biodegradable polymer are completely dissolved, the first mixture contains the biodegradable polymer and the drug at a weight ratio of 2:1 to 9:1. When the weight ratio of the biodegradable polymer and the drug is less than 2:1, that is, when the biodegradable polymer is contained at less than the above weight ratio, the weight ratio of the biodegradable polymer is smaller than the weight ratio of the drug, so that there occurs a problem in that it is difficult to prepare microparticles in a form that the drug is uniformly distributed and contained in the spherical biodegradable polymer particles, and when the weight ratio of the biodegradable polymer and the drug is more than 9:1, that is, when the biodegradable polymer is contained at more than the above weight ratio, the content of the drug in the microparticles is small, so that there occurs a problem in that the microparticles need to be administered in a large amount in order to administer the drug at a desired concentration.

More specifically, the biodegradable polymer is included in an amount of 10 to 20 wt %, preferably 15 wt % in the first mixture, but the amount is not limited to the example.

Step 2) (S200) is a step of preparing a second mixture, and prepares a second mixture by dissolving a surfactant in water. The surfactant can be used without limitation as long as the surfactant can help the biodegradable polymer solution form a stable emulsion. Specifically, the surfactant is one or more selected from the group consisting of a nonionic surfactant, an anionic surfactant, a cationic surfactant, and a mixture thereof, and more specifically, the surfactant is one or more selected from the group consisting of methyl cellulose, polyvinylpyrrolidone, lecithin, gelatin, polyvinyl alcohol, polyoxyethylene sorbitan fatty acid esters, polyoxyethylene castor oil derivatives, sodium lauryl sulfate, sodium stearate, esters, amines, linear diamines, fatty amines, and a mixture thereof, and is preferably polyvinyl alcohol, but the surfactant is not limited to the example.

Step 3) (S300) and Step 4) (S400) are steps of infusing the first mixture and the second mixture into a microchannel formed on a wafer and allowing the first mixture and the second mixture to flow.

More specifically, aluminum is deposited onto a silicon wafer by using an e-beam evaporator, and a photoresist is patterned on aluminum by using a photolithography technique. Thereafter, the wafer is aluminum-etched by using a photoresist as a mask, silicon is etched by deep ion reactive etching (DRIE) by using aluminum as a mask after removing the photoresist, and glass is anodically bonded onto the wafer and hermetically sealed after removing aluminum, thereby manufacturing the aforementioned microchannel.

Further, the aforementioned microchannels have an average diameter of 40 to 100 preferably 40 to 60 and more preferably 50 but the average diameter is not limited to the example. When the microchannels have an average diameter of 40 µm or less, microparticles to be prepared are likely to be prepared as small microparticles having a diameter of 20 µm or less, so that the microparticles are highly likely to be captured by microphages after being infused into the human body, and through this, it is possible to affect the release and in vivo absorption of an effective drug. In addition, when the channels have an average diameter of 100 µm or more, microparticles to be prepared are likely to be prepared as microparticles having a size of 70 µm or more, so that when the injection is administered, a foreign body sensation and pain may be increased, and the particle size distribution of the prepared particles is increased, so that it is difficult to prepare microparticles having a uniform particle size.

In addition, a width (w) of the cross-section and a height (d) of the cross-section of the microchannel are closely associated with an average diameter (d') of microparticles to be prepared. As illustrated in FIG. 6, the width (w) of the cross-section of the microchannel is within a ratio range of 0.7 to 1.3 for an average diameter (d') of the microparticles, and a height (d) of the cross-section of the microchannel is within a ratio range of 0.7 to 1.3 for an average diameter (d') of the microparticles.

That is, when the average diameter (d') of the microparticles to be prepared is determined, it is possible to prepare microparticles with a desired size only when the width (w) and height (d) of the cross-section of the microchannel are set to a ratio range of 0.7 to 1.3 for the d'.

Step 3) (S300) infuses the first mixture into a microchannel in a straight-line direction and allows the first mixture to flow, and Step 4) (S400) infuses the second mixture into a microchannel on both side surfaces or one side surface formed so as to form an intersection point with a microchannel in a straight-line direction, and allows the second mixture to flow.

That is, the first mixture flows along the microchannel in a straight-line direction, and the second mixture flows along the microchannel which forms an intersection point with the microchannel in a straight-line direction on both side surfaces or one side surface based on the microchannel in a straight-line direction, and meets the flow of the first mixture.

In this case, when the first mixture is infused into a microchannel in a straight-line direction, the first mixture is infused under a certain pressure condition and allowed to flow at a certain flow rate, and in this case, the pressure condition is 600 to 1,000 mbar, preferably 800 mbar, but is not limited to the example. Further, when the second mixture is infused into a microchannel on both side surfaces or one side surface, the second mixture is infused under a certain pressure condition and allowed to flow at a certain flow rate, and in this case, the pressure condition is 1,200 to 1,600 mbar, preferably 1,400 mbar, but is not limited to the example.

That is, in order to allow the second mixture forming an intersection point with the flow of the first mixture to flow at a higher flow rate than the first mixture to be infused into the microchannel in a straight-line direction, the second mixture is allowed to flow under a higher pressure condition.

As described above, the second mixture having a relatively higher flow rate compresses the first mixture at a point where the flow of the first mixture and the flow of the second mixture meet each other by varying the flow rates of the first mixture and the second mixture and making the flow rate of the second mixture higher than the flow rate of the first mixture, and in this case, due to repulsive force between the first mixture and the second mixture, the biodegradable polymer and the drug in the first mixture form spherical microparticles, and more specifically, microparticles in a form in which the drug is uniformly distributed in the spherical biodegradable polymer are formed.

Step 5) (S500) is a step of collecting microparticles, and prevents aggregation of initially produced microparticles by collecting the microparticles in a bath comprising the second mixture.

Step 5) (S500) uses the second mixture prepared in Step 2) (S200), that is, a mixed solution of a surfactant and water, and is used to prevent aggregation of collected microparticles by preparing the second mixture in Step 2) (S200), and then infusing a portion of the second mixture into a microchannel, and transferring the other portion to the bath in Step 5) (S500).

Step 6) (S600) is a step of stirring microparticles collected in the bath, and an organic solvent present on the surfaces of the microparticles is evaporated and removed by stirring the microparticles at a predetermined stirring rate under a predetermined temperature condition. In this case, the stirring condition proceeds in an order of firstly stirring the microparticles at a rate of 800 to 1,200 rpm at 14 to 16° C. for 1 to 2 hours; secondly stirring the microparticles at a rate of 800 to 1,200 rpm at 19 to 21° C. for 0.5 to 1.5 hours after the first stirring; and thirdly stirring the microparticles at a rate of 800 to 1,200 rpm at 24 to 26° C. for 0.5 to 1.5 hours after the second stirring. The stirring rate is 800 to 1,200 rpm, preferably 1,000 rpm, but is not limited to the example. The stirring rate at which microparticles are stirred is maintained equally in the first, second, and third stirring, but it is characterized that the microparticles are stirred while gradually increasing the temperature, and as the temperature is increased step by step, the evaporation rate of the organic solvent present on the surfaces of the microparticles may be adjusted. That is, microparticles having smooth surfaces may be prepared by slowly evaporating the organic solvent present on the surfaces of the microparticles.

More specifically, in Step 6) (S600), the microparticles are firstly stirred at 14 to 16° C. for 1 to 2 hours, preferably at 15° C. for 1.5 hours. Thereafter, the microparticles are secondly stirred at 19 to 21° C. for 0.5 to 1.5 hours, preferably at 20° C. for 1 hour. Thereafter, the microparticles are thirdly stirred at 24 to 26° C. for 0.5 to 1.5 hours, preferably at 25° C. for 1 hour.

The temperature at which the first mixture and the second mixture flow in the microchannel is also 14 to 16° C., preferably 15° C. That is, after the mixtures flow in the microchannel and form an intersection point to produce microparticles, the temperature is constantly maintained at a low temperature of 14 to 16° C. until the collected microparticles are firstly stirred. Only when the low temperature is maintained during the process of preparing microparticles, it is possible to prepare and maintain spherical particles. That is, when the process of preparing microparticles is not under the low temperature condition, there occurs a problem in that it is difficult to prepare particles having a predetermined spherical shape.

Finally, Step 7) (S700) is a step of washing the microparticles and drying the microparticles, and the microparticles from which the organic solvent on the surfaces is completely removed by stirring are washed several times with purified water which is sterilized and filtered to remove the surfactant remaining in the microparticles, and are later lyophilized.

The microparticles finally produced are in a form in which the drug is uniformly distributed in the spherical biodegradable polymer microparticles, have an average particle diameter of 20 to 70 and contain the biodegradable polymer and the drug at a weight ratio of 3:1 to 9:1. When the microparticles have an average diameter of less than 20 the microparticles are highly likely to be captured by macrophages after being infused into the human body, and accordingly, the release of the drug from the particles and in vivo absorption of the drug may be affected, and when the particles have an average diameter of more than 70 pain may be increased when the drug included in an injection is administered to a patient to be administered by using a syringe needle having a large gauge.

The weight ratio of the biodegradable polymer and the drug included in the microparticles is the same as the weight ratio in the first mixture, and as the microparticles are prepared and the organic solvent is completely evaporated and removed, it is possible to prepare microparticles containing the biodegradable polymer and the drug in at a ratio which is the same as the weight ratio in the first mixture.

Depending on the type of the drug, there is a difference in the extended release period, and more specifically, the palonosetron which is an antiemetic and minocycline which is an antibiotic may sustain the effects as the antiemetic and the antibiotic because the drug is released for 1 week.

Liraglutide and exenatide for preventing and treating diabetes may sustain the effects of preventing and treating diabetes because the drug is released for 1 week to 1 month.

Olanzapine and aripiprazole for preventing and treating a psychosis may sustain the effects of preventing and treating psychosis because the drug is released for 2 weeks to 1 month.

Donepezil and memantine for preventing and treating dementia and lanreotide and octreotide for preventing and treating acromegaly may sustain the effects of treating dementia and preventing and treating acromegaly because the drug is released for 1 month.

Naltrexone for preventing and treating alcoholism may sustain the effects of preventing and treating alcoholism because the drug is released for 1 month to 3 months.

It can be confirmed that the drug release period varies depending on the type of the drug contained in the microparticles, and the duration of the drug effect associated therewith also varies. For the drugs, microparticles were prepared in consideration of the difference in the retention time in the body according to the use of a drug, and the microparticles according to the preparation method of the present invention vary in the range of the content of the biodegradable polymer and the drug, so that the duration of the drug effect can be arbitrarily adjusted.

More specifically, the weight ratio of the biodegradable polymer and the drug of the microparticles varies depending on the specific drug type.

For the antiemetic palonosetron and the antibiotic minocycline, the content ratio of the biodegradable polymer and the drug is 1.5:1 to 2.5:1, in consideration of the fact that the drug is released for 1 week, and thus the drug effect needs to be sustained.

For liraglutide and exenatide for preventing and treating diabetes, the content ratio of the biodegradable polymer and the drug is 2:1 to 9:1, from the viewpoint that the drug is released for 1 week to 1 month, and thus the drug effect needs to be sustained.

For olanzapine and aripiprazole for preventing and treating a psychosis, the content ratio of the biodegradable polymer and the drug is 4:1 to 9:1, from the viewpoint that drug is released for 2 weeks to 1 month, and thus the drug effect needs to be sustained.

For donepezil and memantine for preventing and treating dementia and lanreotide and octreotide for preventing and treating acromegaly, the content ratio of the biodegradable polymer and the drug is 4:1 to 9:1, from the viewpoint that the drug needs to be released for 1 month and the drug effect needs to be sustained.

For naltrexone for preventing and treating alcoholism, the content ratio of the biodegradable polymer and the drug is 4:1 to 9:1, from the viewpoint that the drug is released for 1 month to 3 months, and thus the effect of preventing and treating alcoholism needs to be sustained.

When the content range of the biodegradable polymer and the drug is less than the minimum range, the weight ratio of the biodegradable polymer is smaller than the weight of the drug, so that there occurs a problem in that it is difficult to prepare microparticles in the form in which the drug is uniformly distributed and contained in the spherical biodegradable polymer particles. Further, when the content range is more than the maximum range, the content of the drug in the microparticles is small, so that there may occur a problem in that a large amount of microparticles need to be administered in order to administer the drug at a desired concentration.

Among the drugs, liraglutide, exenatide, lanreotide, and octreotide are water-soluble drugs and microparticles are prepared by a method different from the aforementioned method for preparing microparticles. Furthermore, even other drugs in addition to the water-soluble drugs may be classified into fat-soluble or water-soluble drugs depending on whether the drugs are bonded to a salt, and when the drugs exhibit characteristics of water-soluble drugs, the microparticles may be prepared by the following method for preparing microparticles.

The preparing of the microparticles may include: 1-1) preparing a first' mixture by dissolving a water-soluble drug in water; 1-2) preparing a second' mixture by dissolving a biodegradable polymer in an organic solvent; 1-3) infusing the first' mixture in Step 1-1) into a microchannel in a straight-line direction and allowing the first' mixture to flow; 1-4) preparing a w/o emulsion in which a water-soluble drug aqueous solution is distributed in a spherical biodegradable polymer organic solvent by infusing the second' mixture in Step 1-2) into a microchannel formed on both side surfaces or one side surface and allowing the second mixture to flow so as to form an intersection point with a microchannel through which the first' mixture in Step 1-3) flows in a straight-line direction, and intersecting a flow of the first mixture in a straight-line direction with a flow of the second' mixture; 1-5) preparing a third' mixture by dissolving a surfactant in water; 1-6) preparing a spherical w/o/w double emulsion by infusing the third' mixture in Step 1-5) into a microchannel formed on both side surfaces or one side surface and allowing the third' mixture to flow so as to form an intersection point with a microchannel through which the w/o emulsion in Step 1-4) flows in a straight-line direction, and intersecting a flow of the w/o emulsion in a straight-line direction with a flow of the third' mixture; 1-7) collecting the w/o/w double emulsion formed at the intersection point in Step 1-6); 1-8) evaporating and removing an organic solvent present in the w/o/w double emulsion collected in Step 1-7) by stirring the double emulsion; and 1-9) washing the microparticles prepared by the w/o/w double emulsion in Step 1-8) and drying the microparticles.

Therefore, since the solutions for dissolving the drug are partially different when the fat-soluble drug is used and when the water-soluble drug is used, a part of the preparation process is added, but the preparations of microparticles in the form in which the drug is uniformly distributed are the same as each other.

As mentioned above, when the water-soluble drug is used, during the infusion of the first' mixture into a microchannel in a straight-line direction, the first' mixture is infused under a certain pressure condition and allowed to flow at a certain flow rate, and in this case, the pressure condition is 600 to 1,000 mbar, preferably 800 mbar, but is not limited to the example. During the infusion of the second' mixture into a microchannel on both side surfaces or one side surface, the second' mixture is infused under a certain pressure condition and allowed to flow at a certain flow rate, and in this case, the pressure condition is 1,200 to 1,600 mbar, preferably 1,400 mbar, but is not limited to the example. Likewise, even in the case of the third mixture infused into a microchannel on both side surfaces or one side surface, during the infusion into the microchannel, the third mixture is infused under a certain pressure condition and allowed to flow at a certain flow rate, and in this case, the pressure condition is 1,200 to 1,600 mbar, preferably 1,400 mbar, but is not limited to the example.

That is, in order to allow a flow of the mixture injected from the side surface so as to form an intersection point to flow at a higher flow rate than the mixture to be infused into the microchannel in a straight-line direction, the mixture is allowed to flow under a higher pressure condition.

As described above, by making the flow rate of the mixture injected from the side surface higher than the flow rate of the mixture flowing in a straight-line direction, the mixture in a side surface direction, which has a relatively higher flow rate compresses the mixture in a straight-line direction at the point where the flow of the mixture in a straight-line direction and the flow of the mixture in a side surface direction meet, and in this case, a spherical w/o/w emulsion may be prepared by the repulsion of the mixture in a straight-line direction and the mixture in a side surface direction.

The microparticles may be prepared by infusing the mixture into the microchannel formed on a wafer and allowing the mixture to flow.

More specifically, aluminum is deposited onto a silicon wafer by using an e-beam evaporator, and a photoresist is patterned on aluminum by using a photolithography technique. Thereafter, the wafer is aluminum-etched by using a photoresist as a mask, silicon is etched by deep ion reactive etching (DRIE) by using aluminum as a mask after removing the photoresist, and glass is anodically bonded onto the wafer and hermetically sealed after removing aluminum, thereby manufacturing the aforementioned microchannel.

The organic solvent of the present invention is an organic solvent which is immiscible with water, is one or more selected from the group consisting of, for example, chloroform, chloroethane, dichloroethane, trichloroethane, and a mixture thereof, and is preferably dichloromethane, but the organic solvent is not limited to the example, and the organic solvent can dissolve a biodegradable polymer, and any organic solvent can be used as long as the organic solvent can be easily selected by a person with ordinary skill in the art without being limited to the aforementioned example.

The surfactant of the present invention can be used without limitation as long as the surfactant can help the biodegradable polymer solution form a stable emulsion. Specifically, the surfactant is one or more selected from the group consisting of a non-ionic surfactant, an anionic surfactant, a cationic surfactant, and a mixture thereof, and more specifically, the surfactant is one or more selected from the group consisting of methyl cellulose, polyvinylpyrrolidone, lecithin, gelatin, polyvinyl alcohol, polyoxyethylene sorbitan fatty acid esters, polyoxyethylene castor oil derivatives, sodium lauryl sulfate, sodium stearate, esters, amines, linear diamines, fatty amines, and a mixture thereof, and is preferably polyvinyl alcohol, but the surfactant is not limited to the example.

Preparation Example: Preparation of Microparticles Comprising Drug

Preparation of microparticles comprising naltrexone

IVL-N1

A first mixture was prepared by dissolving poly(lactide-co-glycolide) (PLGA) and naltrexone in dichloromethane. In this case, poly(lactide-co-glycolide) in the first mixture was contained at a ratio of 15 wt %, and the weight ratio of poly(lactide-co-glycolide) and naltrexone was 4:1.

A second mixture including polyvinyl alcohol in an amount of 0.25 wt % was prepared by mixing a surfactant polyvinyl alcohol with water.

The first mixture and the second mixture were infused into a microchannel formed on a silicon wafer and allowed to flow. In this case, in order to allow the first mixture and the second mixture to flow at a certain flow rate, the first mixture and the second mixture were allowed to flow under a pressure condition of 800 mbar and under a pressure condition of 1,400 mbar, respectively. The temperature condition was maintained at 15° C.

Microparticles produced at an intersection point where the flow of the first mixture and the flow of the second mixture meet each other were collected in a bath comprising the second mixture. The microparticles collected in the bath were firstly stirred at a rate of 1,000 rpm at 15° C. for 1.5 hours, the temperature was increased to 20° C. and the microparticles were secondly stirred at a rate of 1,000 rpm for 1 hour, and the temperature was increased to 25° C. and the microparticles were thirdly stirred at a rate of 1,000 rpm for 1 hour.

The microparticles completely stirred were washed several times with purified water which was sterilized and filtered, and were lyophilized, thereby preparing microparticles.

IVL-N2

Microparticles were prepared in the same manner as in IVL-N1, except that poly(lactide-co-glycolide) and naltrexone were contained at a weight ratio of 9:1.

IVL-N3

Microparticles were prepared in the same manner as in IVL-N1, except that poly(lactide-co-glycolide) and naltrexone were contained at a weight ratio of 2:1.

IVL-N4

Microparticles were prepared in the same manner as in IVL-N1, except that poly(lactide-co-glycolide) and naltrexone were contained at a weight ratio of 12:1.

IVL-N5 to IVL-N9

Microparticles were prepared in the same manner as in IVL-N1, but microparticles were collected in the bath comprising the second mixture, and then the stirring process was performed under the conditions in the following Table 1 as the stirring conditions.

TABLE 1

|  | Stirring condition | Stirring temperature | Stirring time | Stirring rate |
|---|---|---|---|---|
| IVL-N5 | 1 | 15° C. | 1.5 hours | 800 rpm |
|  | 2 |  | 1 hour | 1000 rpm |
|  | 3 |  | 1 hour | 1200 rpm |
| IVL-N6 | 1 | 20° C. | 1.5 hours | 800 rpm |
|  | 2 |  | 1 hour | 1000 rpm |
|  | 3 |  | 1 hour | 1200 rpm |
| IVL-N7 | 1 | 25° C. | 1.5 hours | 800rpm |
|  | 2 |  | 1 hour | 1000 rpm |
|  | 3 |  | 1 hour | 1200 rpm |
| IVL-N8 | 1 | 15° C. | 1.5 hours | 800 rpm |
|  | 2 | 20° C. | 1 hour |  |
|  | 3 | 25° C. | 1 hour |  |
| IVL-N9 | 1 | 15° C. | 1.5 hours | 1200 rpm |
|  | 2 | 20° C. | 1 hour |  |
|  | 3 | 25° C. | 1 hours |  |

Preparation of Microparticles Comprising Memantine

IVL-M1 to IVL-M4

Microparticles were prepared by the same preparation method with the same contents of the biodegradable polymer and the drug as those of IVL-N1 to IVL-N4, except that as the drug, memantine was used instead of naltrexone.

Preparation of Microparticles Comprising Donepezil

IVL-D1 to IVL-D4

Microparticles were prepared by the same preparation method with the same contents of the biodegradable polymer and the drug as those of IVL-N1 to IVL-N4, except that as the drug, donepezil was used instead of naltrexone.

Preparation of Microparticles Comprising Aripiprazole

IVL-A1 to IVL-A4

Microparticles were prepared by the same preparation method with the same contents of the biodegradable polymer and the drug as those of IVL-N1 to IVL-N4, except that as the drug, aripiprazole was used instead of naltrexone.

Preparation of Microparticles Comprising Olanzapine

IVL-Z1 to IVL-Z4

Microparticles were prepared by the same preparation method with the same contents of the biodegradable polymer and the drug as those of IVL-Z1 to IVL-Z4, except that as the drug, olazapine was used instead of naltrexone.

Preparation of Microparticles Comprising Minocycline

IVL-C1

Microparticles were prepared by the same preparation method as IVL-N1, except that as the drug, minocycline was used instead of naltrexone, and the biodegradable polymer and minocycline were contained at a weight ratio of 1.5:1.

IVL-C2

Microparticles were prepared by the same preparation method as IVL-N1, except that as the drug, minocycline was used instead of naltrexone, and the biodegradable polymer and minocyline were contained at a weight ratio of 2.5:1.

IVL-C3

Microparticles were prepared by the same preparation method as IVL-N1, except that as the drug, minocycline was used instead of naltrexone, and the biodegradable polymer and minocyline were contained at a weight ratio of 1:1.

IVL-C4

Microparticles were prepared by the same preparation method as IVL-N1, except that as the drug, minocycline was used instead of naltrexone, and the biodegradable polymer and minocycline were contained at a weight ratio of 3:1.

Preparation of Microparticles Comprising Palonosetron

IVL-P1 to IVL-P4

Microparticles were prepared by the same preparation method with the same contents of the biodegradable polymer and the drug as those of IVL-C1 to IVL-C4, except that as the drug, palonosetron was used instead of minocycline.

Preparation of Microparticles Comprising Octreotide

IVL-O1

A first' mixture was prepared by dissolving octreotide in water. A second' mixture was prepared by dissolving poly (lactide-co-glycolide) (PLGA) in dichloromethane. A third mixture comprising polyvinyl alcohol in an amount of 0.25 wt % was prepared by mixing a surfactant polyvinyl alcohol with water.

The first' mixture, the second' mixture, and the third mixture were infused into a microchannel formed on a silicon wafer and allowed to flow. In this case, in order to allow the first' mixture, the second' mixture, and the third mixture to flow at a certain flow rate, the first mixture, the second mixture, and the third mixture were allowed to flow under a pressure condition of 800 mbar, under a pressure condition of 1,400 mbar, and under a pressure condition of 1,400 mbar, respectively. The temperature condition was maintained at 15° C.

Microparticles produced at an intersection point where the flow of a w/o emulsion formed by intersecting the flow of the first' mixture with the flow of the second' mixture and the flow of the third mixture met each other were collected in a bath comprising the third mixture. The microparticles collected in the bath were firstly stirred at a rate of 1,000 rpm at 15° C. for 1.5 hours, the temperature was increased to 20° C. and the microparticles were secondly stirred at a rate of 1,000 rpm for 1 hour, and the temperature was increased to 25° C. and the microparticles were thirdly stirred at a rate of 1,000 rpm for 1 hour.

The microparticles completely stirred were washed several times with purified water which was sterilized and filtered, and were lyophilized, thereby preparing microparticles.

The biodegradable polymer and octreotide were contained at a content ratio of 4:1 in the microparticles.

IVL-O2

Microparticles were prepared by the same preparation method as in IVL-O1, except that the biodegradable polymer and octreotide were contained at a content ratio of 9:1.

IVL-O3

Microparticles were prepared by the same preparation method as in IVL-O1, except that the biodegradable polymer and octreotide were contained at a content ratio of 2:1.

IVL-O4

Microparticles were prepared by the same preparation method as in IVL-O1, except that the biodegradable polymer and octreotide were contained at a content ratio of 12:1.

Preparation of Microparticles Comprising Lanreotide

IVL-L1 to IVL-L4

Microparticles were prepared by the same preparation method with the same contents of the biodegradable polymer and the drug as those of IVL-O1 to IVL-O4, except that as the drug, lanreotide was used instead of octreotide.

Preparation of Microparticles Comprising Exenatide

IVL-E1

Microparticles were prepared by the same preparation method as IVL-O1, except that as the drug, exenatide was used instead of octreotide, and the biodegradable polymer and exenatide were contained at a weight ratio of 2:1.

IVL-E2

Microparticles were prepared by the same preparation method as IVL-O2, except that as the drug, exenatide was used instead of octreotide.

IVL-E3

Microparticles were prepared by the same preparation method as IVL-O3, except that as the drug, exenatide was used instead of octreotide, and the biodegradable polymer and exenatide were contained at a weight ratio of 1:1.

IVL-E4

Microparticles were prepared by the same preparation method as IVL-O4, except that as the drug, exenatide was used instead of octreotide.

Preparation of Microparticles Comprising Liraglutide

IVL-G1 to IVL-G4

Microparticles were prepared by the same preparation method with the same contents of the biodegradable polymer and the drug as those of IVL-E1 to IVL-E4, except that as the drug, liraglutide was used instead of exenatide.

Experimental Example 1: Study on Shapes of Microparticles

In order to study the shapes of microparticles according to the stirring conditions, the shapes of the microparticles prepared under the conditions in IVL-N1 and IVL-N5 to IVL-N9 were studied through SEM photographs.

The results are shown in the following Table 2.

TABLE 2

| Experiment according to stirring condition | Preparation result of microparticles |
| --- | --- |
| IVL-N5 | Δ |
| IVL-N6 | Δ |
| IVL-N7 | Δ |
| IVL-N8 | ○ |
| IVL-N9 | ○ |
| IVL-N1 | ○ |

A means that the aggregation phenomenon of microparticles occurs due to the effects of the residual solvent and the shapes of the microparticles are uneven as shown in the SEM photographs of FIGS. 2 and 3.

In contrast, in the case of IVL-N1, IVL-N8, and IVL-N9, as shown in the SEM photographs of FIGS. 4 and 5, it was confirmed that the shapes of the microparticles were uniformly formed and no aggregation phenomenon occurred.

That is, during the stirring, it was confirmed that the temperature conditions affected the shapes of the microparticles and the occurrence of the aggregation phenomenon.

In order to prepare microparticles, microparticles were prepared using octreotide, lanreotide, memantine, donepezil, aripiprazole, olanzapine, exenatide, liraglutide, minocycline, and palonosetron instead of naltrexone, and then in spite of following the result of confirming the shapes of the microparticles and the occurrence of aggregation phenomenon according to the difference in stirring condition, by confirming that the same phenomenon as in Table 2 occurred, it was confirmed that the there were differences in the shapes of the microparticles and the occurrence of aggregation phenomenon caused by the difference in stirring condition regardless of the type of drug.

Experimental Example 2: Drug Release Experiment of Microparticles Containing Drug 1. In-Vitro Drug Release Experimental Method About 100 mg of the microparticles were put into a glass test container having a volume of 120 mL, and the container was filled with 100 mL of a release test solution. A drug release experiment was performed by putting the test container into a water bath at 45° C. and reciprocating the test container at an amplitude of 4 cm and a shaking frequency of 120 times/min as an experimental condition for acceleration of drug release. At the time of collecting the sample, the mixture was mixed by shaking the bottle well, and 1 mL of the sample was taken. After the sample was centrifuged at 13,000 rpm for 3 minutes, the supernatant was taken and analyzed with high performance liquid chromatography.

2. Experimental Results (1) Microparticles of IVL-N2

As illustrated in FIG. 7, it was confirmed that the drug was continuously released for 3 months. It was confirmed that even when the initial release amount and the release amount for 3 months were compared, the drug exhibited a significant release amount enough to maintain the effect.

(2) Microparticles of IVL-O2, IVL-L2, IVL-M2, and IVL-D2

As illustrated in FIG. 8, it was confirmed that the drug was continuously released for 1 month. It was confirmed that even when the initial release amount and the release amount for 1 month were compared, the drug exhibited a significant release amount enough to maintain the effect.

(3) Microparticles of IVL-A2 and IVL-Z2

As illustrated in FIG. 9, it was confirmed that the drug was continuously released for 2 weeks. It was confirmed that even when the initial release amount and the release amount for 2 weeks were compared, the drug exhibited a significant release amount enough to maintain the effect.

(4) Microparticles of IVL-E2, IVL-G2, IVL-C2, and IVL-P2

As illustrated in FIG. 10, it was confirmed that the drug was continuously released for 1 week. It was confirmed that even when the initial release amount and the release amount for 1 week were compared, the drug exhibited a significant release amount enough to maintain the effect.

While preferred embodiments of the present invention have been described in detail hereinabove, it is to be understood that the scope of the present invention is not limited thereto, and various modifications and improvements made by those skilled in the art using basic concepts of the present invention, which are defined in the following claims also fall within the scope of the present invention.

The invention claimed is:

1. A method for preparing extended release microparticles comprising a drug, the method comprising:
   1) preparing a first mixture by dissolving a biodegradable polymer and a drug in an organic solvent;
   2) preparing a second mixture by dissolving a surfactant in water;
   3) infusing the first mixture in Step 1) into a microchannel in a straight-line direction and allowing the first mixture to flow;
   4) preparing microparticles in a form in which the drug is uniformly distributed in spherical biodegradable polymer particles by infusing the second mixture in Step 2) into a microchannel formed on both side surfaces or one side surface and allowing the second mixture to flow so as to form an intersection point with a microchannel through which the first mixture in Step 3) flows in a straight-line direction, and intersecting a flow of the first mixture in a straight-line direction with a flow of the second mixture;
   5) collecting the microparticles produced at the intersection point in Step 4);
   6) evaporating and removing an organic solvent present in the microparticles collected in Step 5) by stirring the microparticles; and
   7) washing the microparticles in Step 6) and drying the microparticles,
   wherein the drug is selected from the group consisting of palonosetron, minocycline, liraglutide, exenatide, olanzapine, aripiprazole, donepezil, memantine, lanreotide, octreotide, and naltrexone, wherein Step 6) comprises:
6-1) firstly stirring the microparticles at a rate of 800 to 1,200 rpm at 14 to 16° C. for 1 to 2 hours;
6-2) secondly stirring the microparticles at a rate of 800 to 1,200 rpm at 19 to 21° C. for 0.5 to 1.5 hours after the first stirring; and
6-3) thirdly stirring the microparticles at a rate of 800 to 1,200 rpm at 24 to 26° C. for 0.5 to 1.5 hours after the second stirring.

* * * * *